US012109552B2

(12) United States Patent
An et al.

(10) Patent No.: US 12,109,552 B2
(45) Date of Patent: Oct. 8, 2024

(54) CATALYST WITH A CORE-SHELL STRUCTURE FOR METHANE OXIDATION, METHOD OF PREPARING THE SAME AND METHOD OF OXIDIZING METHANE USING THE SAME

(71) Applicants: AJOU UNIVERSITY INDUSTRY—ACADEMIC COOPERATION FOUNDATION, Suwon-si (KR); UNIST (Ulsan National Institute of Science and Technology), Ulsan (KR)

(72) Inventors: Kwang Jin An, Ulsan (KR); Eun Duck Park, Seoul (KR); Eui Seob Yang, Ulsan (KR)

(73) Assignees: AJOU UNIVERSITY INDUSTRY-ACADEMIC COOPERATION FOUNDATION, Suwon-si (KR); UNIST (Ulsan National Institute of Science and Technology), Ulsan (KR)

( * ) Notice: Subject to any disclaimer, the term of this patent is extended or adjusted under 35 U.S.C. 154(b) by 682 days.

(21) Appl. No.: 17/281,773

(22) PCT Filed: Jul. 26, 2019

(86) PCT No.: PCT/KR2019/009370
§ 371 (c)(1),
(2) Date: Mar. 31, 2021

(87) PCT Pub. No.: WO2020/071625
PCT Pub. Date: Apr. 9, 2020

(65) Prior Publication Data
US 2021/0387166 A1 Dec. 16, 2021

(30) Foreign Application Priority Data
Oct. 4, 2018 (KR) .................. 10-2018-0118267

(51) Int. Cl.
*B01J 23/22* (2006.01)
*B01J 21/04* (2006.01)
(Continued)

(52) U.S. Cl.
CPC ............... *B01J 23/22* (2013.01); *B01J 21/04* (2013.01); *B01J 21/08* (2013.01); *B01J 35/19* (2024.01);
(Continued)

(58) Field of Classification Search
CPC .......... C07C 47/04; C07C 45/33; B01J 21/04; B01J 21/08; B01J 23/22; B01J 35/19; B01J 35/40; B01J 37/024
See application file for complete search history.

(56) References Cited

FOREIGN PATENT DOCUMENTS

JP        58-92630 A      6/1983
JP        2000-342964 A   12/2000

OTHER PUBLICATIONS

Shaohong, Z., et al., Thermally stable core—shell Ni/nanorod-CeO2@SiO2 catalyst for partial oxidation of methane at high temperatures, Royal Society of Chemistry, 10, pp. 14031-14038 (Year: 2018).*

(Continued)

*Primary Examiner* — Yate' K Cutliff
(74) *Attorney, Agent, or Firm* — Sughrue Mion, PLLC

(57) ABSTRACT

A catalyst with a core-shell structure for methane oxidation, a method of preparing the catalyst, and a method of methane oxidation using the catalyst are disclosed. The catalyst includes a core structure consisting of a nano-support and core nanoparticles; and a shell coating layer coated on the core structure in which the core nanoparticles have a particle diameter smaller than that of the nano-support and are coated on the nano-support to form a core structure. The catalyst has excellent thermal stability during methane oxi- (Continued)

dation reaction at high temperature and an effect of increasing methane conversion and formaldehyde selectivity.

15 Claims, 17 Drawing Sheets

(51) Int. Cl.
*B01J 21/08* (2006.01)
*B01J 35/00* (2006.01)
*B01J 35/40* (2024.01)
*B01J 37/02* (2006.01)
*B01J 37/10* (2006.01)
*C07C 45/33* (2006.01)
*C07C 47/04* (2006.01)

(52) U.S. Cl.
CPC ............ *B01J 35/40* (2024.01); *B01J 37/0238* (2013.01); *B01J 37/024* (2013.01); *B01J 37/10* (2013.01); *C07C 45/33* (2013.01); *C07C 47/04* (2013.01)

(56) References Cited

OTHER PUBLICATIONS

Nguyen, L. D., et al., Study of new catalyst based on vanadium oxide supported on mesoporous silica for the partial oxidation of methane to formaldehyde: Catalytic properties and reaction mechanism, Journal of Catalysis, vol. 237, pp. 38-48 (Year: 2005).*

Zhu, S., et al., Thermally stable core-shell Ni./nanorod-Ce)2@SiO2 catalyst for partial oxidation of methane at high temperatures, Royal Society of Chemistry, Nanoscale, vol. 10, pp. 14031-14038 (Year: 2018).*

Shaohong Zhu et al., "Thermally stable core-shell Ni/nanorod-Ce02@Si02 catalyst for partial oxidation of methane at high temperatures", Royal Society of Chemistry, Nanoscale, 2018, pp. 14031-14038, vol. 10.

Lucie D. Nguyen et al., "Study of new catalysts based on vanadium oxide supported on mesoporous silica for the partial oxidation of methane to formaldehyde: Catalytic properties and reaction mechanism", Journal of Catalysis, 2006, p. 38-48, vol. 237 (available online Nov. 18, 2005).

Yoon Seok Jung et al., "Enhanced Stability of $LiCoO_2$ Cathodes in Lithium-Ion Batteries Using Surface Modification by Atomic Layer Deposition", Journal of The Electrochemical Society, 2010, pp. A75-A81, vol. 157, No. 1 (published Nov. 18, 2009).

Chen Chen et al., "Methane Oxidation on $Pd@ZrO_2/Si-Al_2O_3$ Is Enhanced by Surface Reduction of $ZrO_2$", ACS Catalysis, 2014, pp. 3902-3909, vol. 4.

Euiseob Yang et al., "$SiO_2@V_2O_5@Al_2O_3$ core-shell catalysts with high activity and stability for r methane oxidation to formaldehyde", Journal of Catalysis, Oct. 18, 2018, pp. 134-144, vol. 368.

International Searching Authority, International Search Report for PCT/KR2019/009370 dated Nov. 5, 2019 (PCT/ISA/210).

International Searching Authority, Written Opinion for PCT/KR2019/009370 dated Nov. 5, 2019 (PCT/ISA/237).

Shaohong Zhu et al., "Thermally stable core-shell Ni/nanorod-$CeO_2$@SiO2 catalyst for partial oxidation of methane at high temperatures", Nanoscale, Jun. 27, 2018, Issue 29 (3 pages total).

* cited by examiner

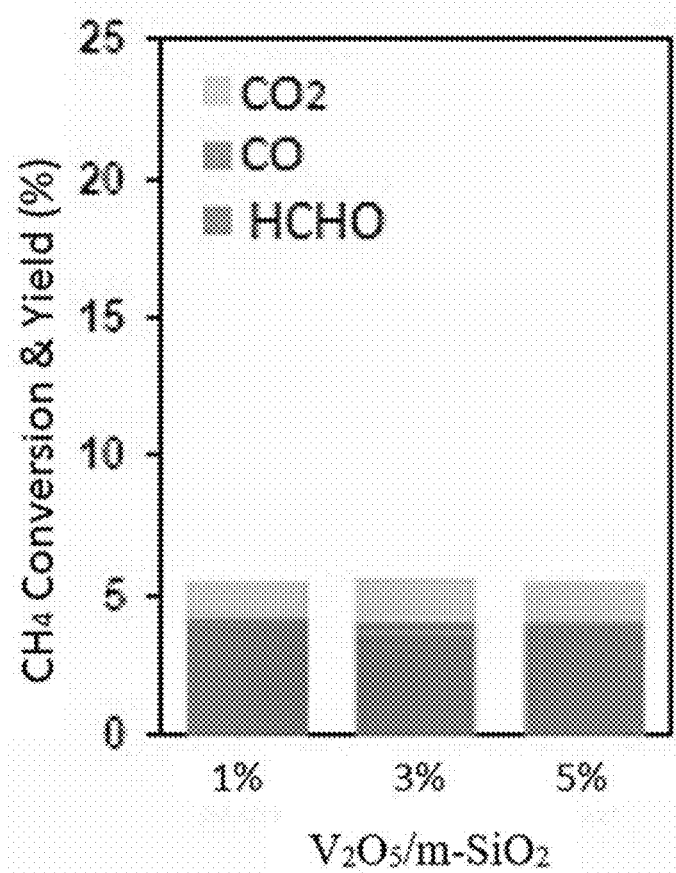

FIG. 6

| Catalyst | ALD cycle no. | Conversion (%) | TOF (s$^{-1}$) | Selectivity (%) | | |
|---|---|---|---|---|---|---|
| | | | | HCHO | CO | CO$_2$ |
| SiO$_2$@V$_2$O$_5$ | 0 | 1.7 | 0.02 | n.d. | 0 | 0 |
| SiO$_2$@V$_2$O$_5$@Al$_2$O$_3$-(*10*) | 10 | 2.0 | 0.02 | n.d. | 0 | 0 |
| SiO$_2$@V$_2$O$_5$@Al$_2$O$_3$-(*30*) | 30 | 1.0 | 0.01 | n.d. | 0 | 0 |
| SiO$_2$@V$_2$O$_5$@Al$_2$O$_3$-(*40*) | 40 | 12.9 | 0.10 | 68 | 19 | 13 |
| SiO$_2$@V$_2$O$_5$@Al$_2$O$_3$-(*50*) | 50 | 22.2 | 0.14 | 58 | 27 | 15 |
| SiO$_2$@V$_2$O$_5$@Al$_2$O$_3$-(*70*) | 70 | 18.7 | 0.13 | 62 | 25 | 13 |
| SiO$_2$@V$_2$O$_5$@Al$_2$O$_3$-(*100*) | 100 | 3.7 | 0.04 | 100 | 0 | 0 |
| V$_2$O$_5$/m-SiO$_2$ 1 wt% | | 5.5 | 0.03 | 71 | 6 | 23 |
| V$_2$O$_5$/m-SiO$_2$ 3 wt% | | 5.6 | 0.03 | 66 | 7 | 27 |
| V$_2$O$_5$/m-SiO$_2$ 5 wt% | | 5.5 | 0.03 | 67 | 8 | 25 |

CATALYST WITH A CORE-SHELL STRUCTURE FOR METHANE OXIDATION, METHOD OF PREPARING THE SAME AND METHOD OF OXIDIZING METHANE USING THE SAME

CROSS REFERENCE TO RELATED APPLICATIONS

This application is a National Stage of International Application No. PCT/KR2019/009370 filed Jul. 26, 2019, claiming priority based on Korean Patent Application No. 10-2018-0118267 filed Oct. 4, 2018.

TECHNICAL FIELD

The present invention relates to a catalyst with a core-shell structure for methane oxidation, a method of preparing the same, and a method of methane oxidation using the same.

BACKGROUND ART

Methane, the main component of natural gas, is mainly used for heating and electricity generation. The recent progress in shale gas collection technology based on hydraulic fracturing presents a further stimulus for converting abundant methane to more valuable chemical feedstocks and thus reducing the dependency on petroleum resources. Nevertheless, the four strong C—H bonds of methane (bond energy=413 kJ mol$^{-1}$) present a serious obstacle to its chemical conversion of methane to useful chemicals. At elevated temperatures for breaking the strong C—H bond of methane, methane can be catalytically converted to syngas that can be used as a feedstock for the catalytic production of added-value hydrocarbons or alcohols. Although a number of indirect processes for the oxidative conversion of methane to formaldehyde (HCHO), methanol ($CH_3OH$), and ethylene ($C_2H_4$) have been developed and applied industrially, direct conversion of methane by partial oxidation is still challenging in view of the abovementioned high C—H bond energy and the need to avoid the production of carbon dioxide as an undesired greenhouse gas. Therefore, the partial oxidation of methane to avoid generation of carbon dioxide by the complete oxidation reaction and to produce high value-added chemicals is very important and remains a challenging task.

In order to produce formaldehyde from methane, a temperature of 600° C. or higher is required to break the strong C—H bond, and $V_2O_5$ and $MoO_3$ are used as the optimum partial oxidation catalyst for producing HCHO or $CH_3OH$. However, because HCHO easily undergoes further oxidation to CO and $H_2O$, it is essential to develop efficient partial oxidation catalysts having high selectivity and high methane conversion. In addition, the use of noble metals such as Pt or Pd for C—H bond activation have good catalytic activity, but results in the complete oxidation of methane to CO, $CO_2$, and $H_2O$, and deactivation of the noble metal catalyst degrades process efficiency. For these reasons, the partial oxidation of methane to HCHO is still regarded as a challenging reaction, and the best methane-to-HCHO conversion achieved so far at 600° C. is less than 10%.

Therefore, it is important to develop a catalyst which is stable at high temperature and can increase the conversion of formaldehyde produced by partial oxidation of methane.

DISCLOSURE

Technical Problem

It is an object of the present invention to provide a highly active vanadium-based catalyst for methane oxidation which is stable at high temperature and increases the production of formaldehyde by methane partial oxidation and a method of preparing the same.

Another object of the present invention is to provide a method of methane oxidation using the catalyst for methane oxidation according to the above preparation method.

Technical Solution

In order to achieve the above object, the present invention provides a catalyst for methane oxidation comprising a core structure consisting of a nano-support and core nanoparticles; and a shell coating layer coated on the core structure, wherein the core nanoparticles have a particle diameter smaller than that of the nano-support and are coated on the nano-support to form a core structure.

Also, the present invention provides a method of preparing a catalyst for methane oxidation comprising preparing nano-supports comprising $SiO_2$; preparing a core structure by hydrothermal reaction of $V_2O_5$ nanoparticles on the nano-supports; and forming a core-shell nanostructure by atomic layer deposition of $Al_2O_3$ on the core structure.

In addition, the present invention provides a catalyst for methane oxidation, which is prepared by the method of preparing the catalyst for methane oxidation.

Furthermore, the present invention provides a method of methane oxidation, comprising reacting methane and oxygen in the presence of the catalyst for methane oxidation.

In addition, the present invention provides a method of methane oxidation for producing formaldehyde comprising producing formaldehyde (HCHO) by reacting methane and oxygen at 500 to 800° C. in the presence of the catalyst for methane oxidation.

Advantageous Effects

The catalyst for methane oxidation according to the present invention has an excellent thermal stability because the $Al_2O_3$ shell prevents aggregation and structural deformation of the $V_2O_5$ nanoparticles even at a high temperature due to the core-shell structure.

In addition, the catalyst for methane oxidation having a core-shell structure according to the present invention formed a new catalyst species between $V_2O_5$ and $Al_2O_3$, so that the conversion of methane and the selectivity of formaldehyde were 22.2% and 57.8%, respectively, even at high temperatures thereby having superior catalyst activity.

DESCRIPTION OF DRAWINGS

FIG. 5c shows methane oxidation performances of V$_2$O$_5$/m-SiO$_2$ catalysts with vanadium loadings of 1, 3, and 5 wt %.

FIG. 6 shows methane oxidation performances of selected vanadium-based catalysts obtained at a CH$_4$/O$_2$ ratio of 1:1 (v/v) and a reaction temperature of 600° C. (n.d.=not detected). Each reaction was conducted more than 3 times for reproducibility and the conversion and turnover frequency (TOF) are mean values and the deviation is within 15%.

BEST MODE

Figure 1A:
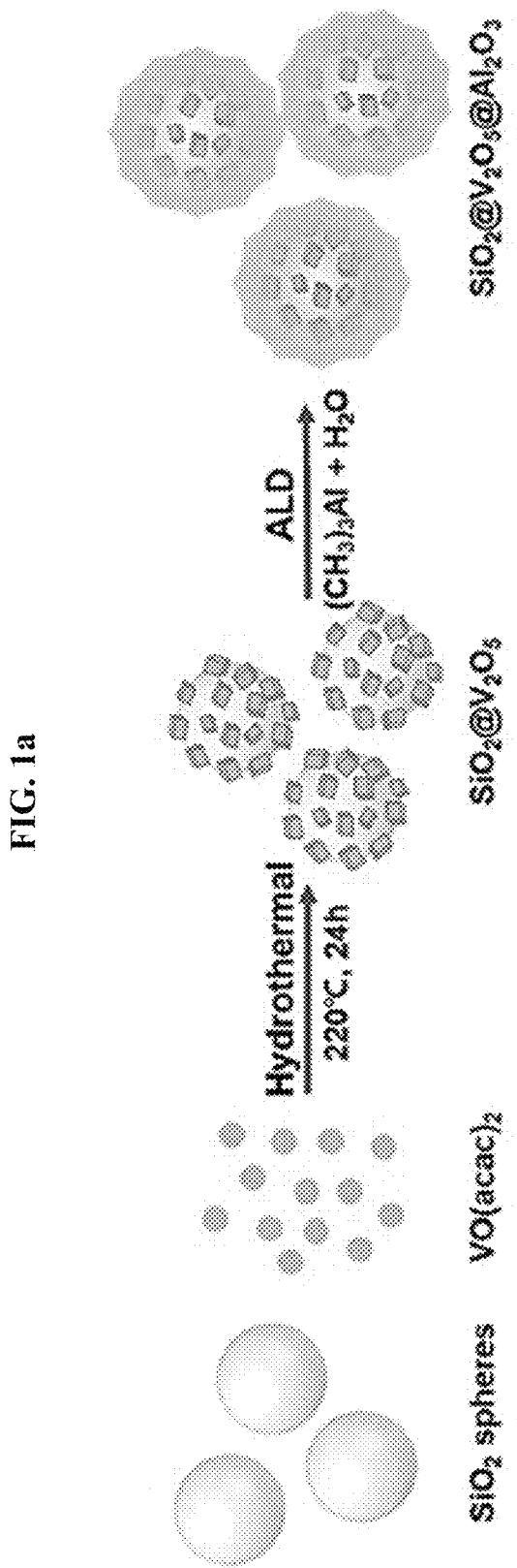
FIG. 1a shows schematic preparation of $SiO_2$@$V_2O_5$@$Al_2O_3$ core@shell nanostructures.

Hereinafter, the present invention will be described in detail.

The present inventors have prepared a nanostructure catalyst having a SiO$_2$@V$_2$O$_5$@Al$_2$O$_3$ core-shell structure which is stable at a high temperature in methane oxidation reaction and excellent in conversion of methane and selectivity to formaldehyde and they have found out that the prepared catalyst has excellent thermal stability at high temperature by Al$_2$O$_3$ because the agglomeration and structural deformation of V$_2$O$_5$ nanoparticles was prevented and forms a new catalyst species between V$_2$O$_5$ and Al$_2$O$_3$ thereby having superior catalytic activity even at high temperatures and have completed the present invention.

The present invention provides a catalyst for methane oxidation comprising: a core structure consisting of a nano-support and core nanoparticles; and a shell coating layer coated on the core structure, wherein the core nanoparticles have a particle diameter smaller than that of the nano-support and are coated on the nano-support to form a core structure.

At this time, the nano-support may be spherical nano-support and comprise SiO$_2$, the core nanoparticles coated on the nano-support may comprise V$_2$O$_5$ having an average particle size of 10 to 100 nm and the shell coating layer coated on the core structure may comprise Al$_2$O$_3$.

Also, the present invention provides a method of preparing a catalyst for methane oxidation comprising: preparing nano-supports comprising SiO$_2$; preparing a core structure by hydrothermal reaction of V$_2$O$_5$ nanoparticles on the nano-supports; and forming a core-shell nanostructure by atomic layer deposition of Al$_2$O$_3$ on the core structure.

At this time, the nano-support may be spherical nano-support and the hydrothermal reaction may be performed at 100 to 250° C. for 5 to 30 hours, preferably at 220° C. for 24 hours.

At this time, when it fails to fall within the above conditions, the V$_2$O$_5$ nanoparticles are not sufficiently coated on the spherical SiO$_2$, so that the interaction with the Al$_2$O$_3$ shell cannot be properly performed, resulting in poor catalytic activity or the yield of the V$_2$O$_5$ nanoparticle coating may be poor in respect of the reaction time, which may lead to an economical problem.

In addition, the atomic layer deposition may be performed by using trimethylaluminum and H$_2$O for 1 to 100 cycles, preferably 50 cycles.

Furthermore, the present invention provides a catalyst for methane oxidation, which is prepared by the method of preparing the catalyst for methane oxidation.

In addition, the present invention provides a method of methane oxidation, comprising reacting methane and oxygen in the presence of the catalyst for methane oxidation.

In addition, the present invention provides a method of methane oxidation for producing formaldehyde comprising producing formaldehyde by reacting methane and oxygen at 500 to 800° C. in the presence of the catalyst for methane oxidation. Preferably, methane and oxygen are reacted at 600° C. in the presence of the catalyst for methane oxidation to produce formaldehyde.

Hereinafter, the present invention will be described in detail with reference to the following examples. It should be noted, however, that the examples of the present invention are provided to more specifically describe the present invention and are not intended to limit the scope of the present invention to those skilled in the art.

<Example 1> Preparation of SiO$_2$@V$_2$O$_5$ Nanostructure

NH$_4$OH (7.5 mL) and H$_2$O (24 mL) were dispersed in ethanol (294 mL). Tetraethyl orthosilicate (TEOS; Aldrich, 98%, 15 mL) was dropwise added to the obtained solution, and the reaction mixture was further stirred for 24 h. The resulting opaque solution was filtered, and the filter cake was washed with ethanol and dried at 70° C. to afford silica spheres. To synthesize SiO$_2$@V$_2$O$_5$ core@shell nanostructures, as-prepared silica spheres (0.3 g) were mixed with vanadyl acetylacetonate (VO(acac)$_2$; Sigma-Aldrich, 97%, 0.83 g) in dimethylformamide (40 mL) upon 3-h sonication. The obtained dispersion was placed in a 50-mL Teflon-lined autoclave reactor and heated at 220° C. for 24 h. The dark precipitate was separated by centrifugation, washed with ethanol, dried at 70° C., and calcined at 400° C. for 3 h to afford SiO$_2$@V$_2$O$_5$ core@shell nanostructures.

<Example 2> Preparation of SiO$_2$@V$_2$O$_5$@Al$_2$O$_3$-(x) (x=10, 30, 40, 50, 70, and 100) Core@Shell Nanostructures Al$_2$O$_3$ shells were grown on SiO$_2$@V$_2$O$_5$ core@shell structures in a rotary ALD reactor using a TMA (trimethyl-aluminum, Sigma-Aldrich, 97%; alumina precursor)—H$_2$O—Ar sequence. First, SiO$_2$@V$_2$O$_5$ powders were loaded into a porous stainless-steel cylinder that was rotated at 140 rpm inside the reaction chamber. For a single cycle of the ALD sequence, TMA introduced at a pressure of 1 Torr was deposited onto $V_2O_5$ surfaces at 180° C., and the chamber was subsequently evacuated to remove $CH_4$ generated as a by-product and unreacted TMA. The chamber was filled with Ar to a pressure of 20 Torr and evacuated after several minutes. Then, $H_2O$ (1 Torr) was introduced to replace the methyl groups of the attached TMA with OH groups, and the chamber was evacuated to remove the produced $CH_4$ and excess $H_2O$ and purged with Ar (20 Torr). For the second cycle, the above steps were repeated. The number of cycles was denoted as (x) and was found to be proportional to the thickness of $Al_2O_3$ shells. $SiO_2@V_2O_5@Al_2O_3$-(x) core@shell nanostructures with controlled $Al_2O_3$ shell thickness were prepared using different numbers of ALD cycles (x=10, 30, 40, 50, 70, and 100).

<Example 3> Preparation of Mesoporous Silica-Supported $V_2O_5$ ($V_2O_5$/m-$SiO_2$) Catalysts Conventional $V_2O_5$/m-$SiO_2$ catalysts were prepared by incipient wetness impregnation. Mesoporous silica with a mesocellular structure (MCF-17) prepared by a previously described method was used as a support. Briefly, 1,3,5-trimethylbenzene (Sigma-Aldrich, 98%; 4 g) was dissolved in 75 mL of an aqueous solution containing 4 g of Pluronic P123 triblock copolymer (Aldrich, average Mw 5800 Da) and 10 mL of concentrated HCl. The reaction mixture was stirred at 40° C. for 2 h and then treated with TEOS (9.2 mL) and maintained for 5 min. The resulting solution was kept at 40° C. for 20 h without stirring, treated with $NH_4F$ (Sigma-Aldrich, 98%; 46 mg), and further aged in a closed bottle at 100° C. for another 24 h. The obtained white precipitate was filtered, washed with water and ethanol, and calcined in air at 600° C. for 6 h to afford mesoporous silica MCF-17. $V_2O_5$/m-$SiO_2$ catalysts were prepared by exposing MCF-17 (1 g) to a solution of ammonium vanadium oxide ($NH_4VO_3$, Alfa Aesar, 99%) in the presence of oxalic acid dihydrate ($C_2H_2O_4 \cdot 2H_2O$, Acros Organics, 99%) overnight. Centrifugation followed by drying afforded solid $V_2O_5$/m-$SiO_2$ catalysts with vanadium precursor loadings of 1, 3, and 5 wt % after calcination at 350° C. for 4 h. Conventional $V_2O_5$/$Al_2O_3$ catalysts were also prepared by the same impregnation method in the presence of commercial $Al_2O_3$(Puralox SBa 200, Sasol) for comparison. For details, 1 g of $Al_2O_3$ was mixed with oxalic acid dihydrate in an ethanol solution of $NH_4VO_3$. After drying at 60° C. and calcination at 350° C. 4 h, 3 and 5 wt % of $V_2O_5$/$Al_2O_3$ catalysts were obtained.

<Example 4> Characterization

In situ XRD patterns were acquired in a 2θ range of 20–80° (Cu Kα radiation, λ=1.5418 Å) using PAnalytical X'Pert Pro and Rigaku SmartLab X-ray diffractometers, respectively. Prior to measurements, samples were loaded on a holder and preheated at 150° C. for 30 min in an Ar atmosphere. In situ spectra were recorded for catalysts exposed to a heated gas mixture of 4% $CH_4$, 4% $O_2$, and balance Ar in steps of 50° C. (from 100 to 800° C.) using a specially constructed cell. Brunauer-Emmett-Teller (BET) surface areas were determined from $N_2$ adsorption/desorption isotherms recorded on a microtrac BELsorp-Max analyzer. Pore size distributions were determined by the Barrett-Joyner-Halenda method. SEM imaging was performed using a Hitachi S-4800 microscope, and TEM imaging was performed using a JEOL JEM-2100F instrument operated at 200 kV. An EDS (energy-dispersive X-ray spectroscopy) analyzer was used for elemental analysis (Oxford instrument, X-Max 80 T). TPR (temperature-programmed reduction) was carried out on the Micromeritics AutoChem II 2920 instrument. Typically, a catalyst sample (100 mg) was loaded into a U-shaped quartz tube and outgassed under He flow at 150° C. for 30 min. Subsequently, the temperature was increased to 800° C. at a rate of 10° C. $min^{-1}$ in a flow of 10% $H_2$ in He (50 mL $min^{-1}$). The amount of consumed $H_2$ was determined by gas chromatography using a Delsi Nermag thermal conductivity detector. Diffuse reflectance UV-vis spectra were recorded at a scan step of 1 nm on an Agilent Cary 5000 UV-vis-NIR spectrophotometer operated in the region of 200-2200 nm. A halon white (PTFE) reflectance standard was used as a reference background. Raman spectra were collected utilizing a WITec alpha300 R spectrometer equipped with a 532-nm diode laser. The laser power was set to 0.1 mW. To obtain sufficient signal-to-noise ratios, spectra were obtained using CCD with 10-sec exposure and 10-fold accumulation.

<Example 5> Methane Oxidation Reaction

Catalytic methane oxidation was conducted in a laboratory-scale flow reactor at atmospheric pressure and a constant temperature of 600° C. As-synthesized vanadium-based catalysts were pelletized and sieved to a particle size of 150-250 μm. A 100 mg catalyst sample was loaded into a quartz tube (inner diameter=1 cm) together with 1 g of purified sand. $CH_4$ (99.95%) and $O_2$ (99.995%) in a 1:1 v/v ratio were fed from the top to the bottom of the catalyst bed at a rate of 40 sccm using mass flow controllers, and the gas hourly space velocity (GHSV) was maintained at 24,000 mL $g_{cat}^{-1} h^{-1}$. The reactor was heated to 600° C. in a furnace and equipped with an inserted thermocouple to monitor temperature. Products were monitored using an online gas chromatograph (YL6500) equipped with Porapak-N and molecular sieve columns connected to both thermal conductivity detector (TCD) and flame ionization detectors (FID) with a methanizer (Ar was flown in as a reference). HCHO, CO, $CO_2$, and $H_2$ were identified as the main reaction products. The products converted from methane were condensed and separated by a cold trap apparatus before entering the gas chromatography. This solution was mixed with 1 M $Na_2SO_3$ solution and the concentration of HCHO was determined by titrating with NaOH and $H_2SO_4$. Methane conversion was calculated as the ratio of consumed and original methane amounts using gas chromatography data for points in stabilized areas with maximum activity values. Selectivity was calculated as the ratio of product amount and total converted methane amount. The conversion of $SiO_2@V_2O_5@Al_2O_3$-(x) core@shell nanostructures (x=40, 50, and 70) was determined by the average value of methane conversions, in which each reaction was conducted more than 3 times for reproducibility. The turnover frequency ($TOF_{HCHO}$) was calculated by the number of $CH_4$ molecules reacted to HCHO on each available vanadium site per time. By assuming that an isolated vanadium species on the outermost surface of the $V_2O_5$ nanoparticles was contacted with the alumina shell, the total surface area of the core@shell catalyst was determined by the size and mass of the structure. The number of core@shell nanostructures was estimated by the mass of single nanoparticle, thus the total surface area and the isolated surface vanadium sites ($7.3 \times 10^{18}$) were finally determined for the TOFs.

Figure 1B:
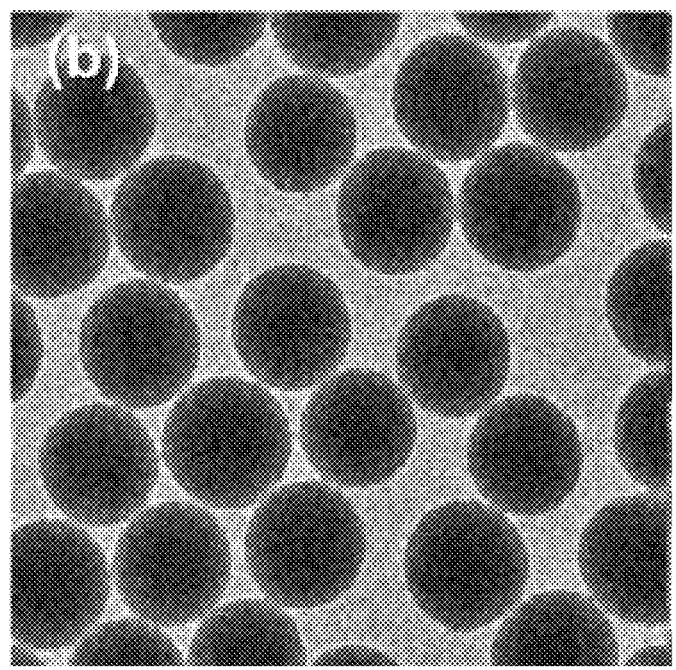
FIG. 1b, FIG. 1c, and FIG. 1d are transmission electron microscopy (TEM) images of $SiO_2$ spheres, $SiO_2$@$V_2O_5$, and $SiO_2$@$V_2O_5$@$Al_2O_3$-(50) core@shell nanostructures, respectively.
Figure 1C:
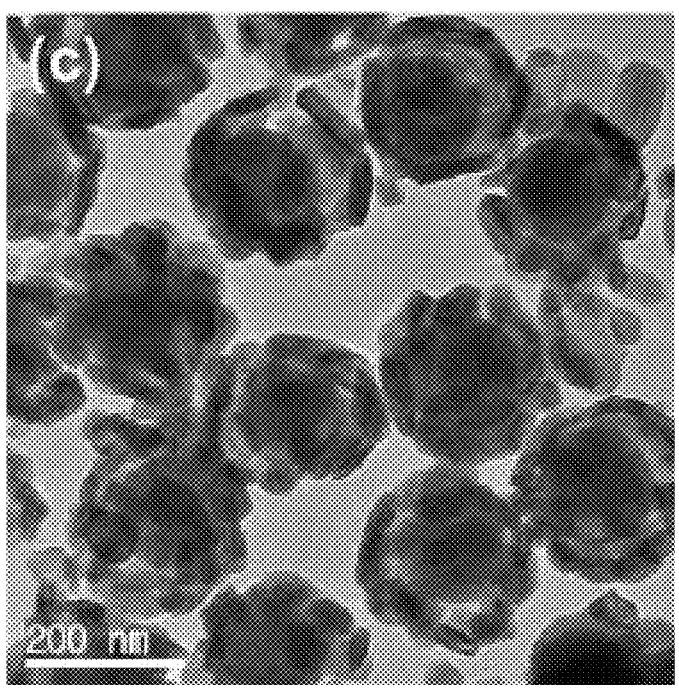
Figure 1D:
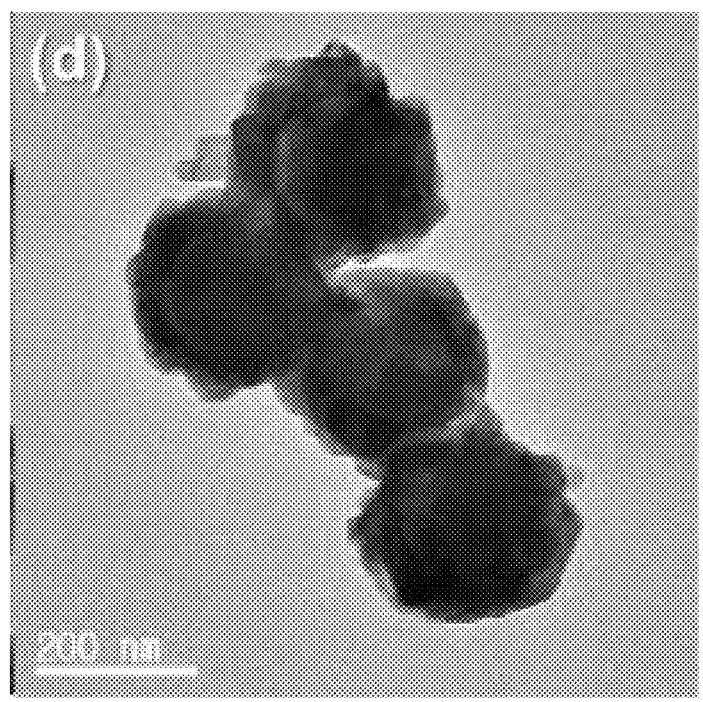

<Experimental Example 1> Preparation of $SiO_2@V_2O_5@Al_2O_3$ Core@Shell Catalysts As a method of Example 2, $SiO_2@V_2O_5@Al_2O_3$ core@shell nanostructures were prepared by hydrothermal synthesis followed by ALD (FIG. 1a), and SiO$_2$ spheres with an average size of 150 nm were synthesized by the method of Example 1 (FIG. 1b). Discrete V$_2$O$_5$ nanoparticles with an average size of 35 nm were deposited on the surface of SiO$_2$ spheres by a hydrothermal reaction in the presence of VO(acac)$_2$ (FIG. 1c). During the reaction, small vanadium clusters were first formed by nucleation, and then the vanadium species were mostly attached to SiO$_2$ spheres, because of the hydrophilic nature of the SiO$_2$ surface. By the subsequent ALD with the various number of repeating cycles, thin Al$_2$O$_3$ layers were deposited over SiO$_2$@V$_2$O$_5$ core@shells with a controlled thickness. FIG. 1d shows a TEM image of representative SiO$_2$@V$_2$O$_5$@Al$_2$O$_3$-(50) core@shell nanostructures, unambiguously demonstrating the presence of Al$_2$O$_3$ layers coating the core structures.

Figure 2A:
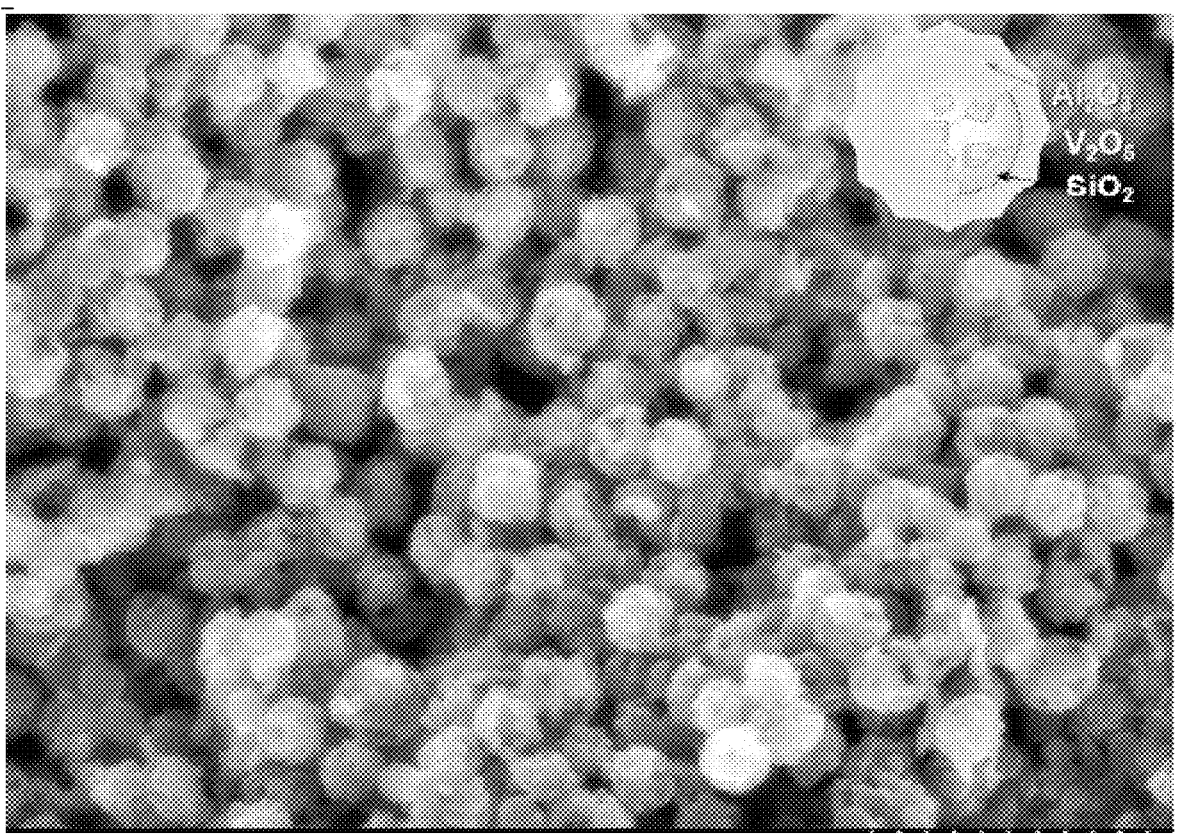
FIG. 2a is an scanning electron microscopy (SEM) image showing structural characterization of $SiO_2$@$V_2O_5$@$Al_2O_3$-(50) core@shell nanostructures.
Figure 2B:
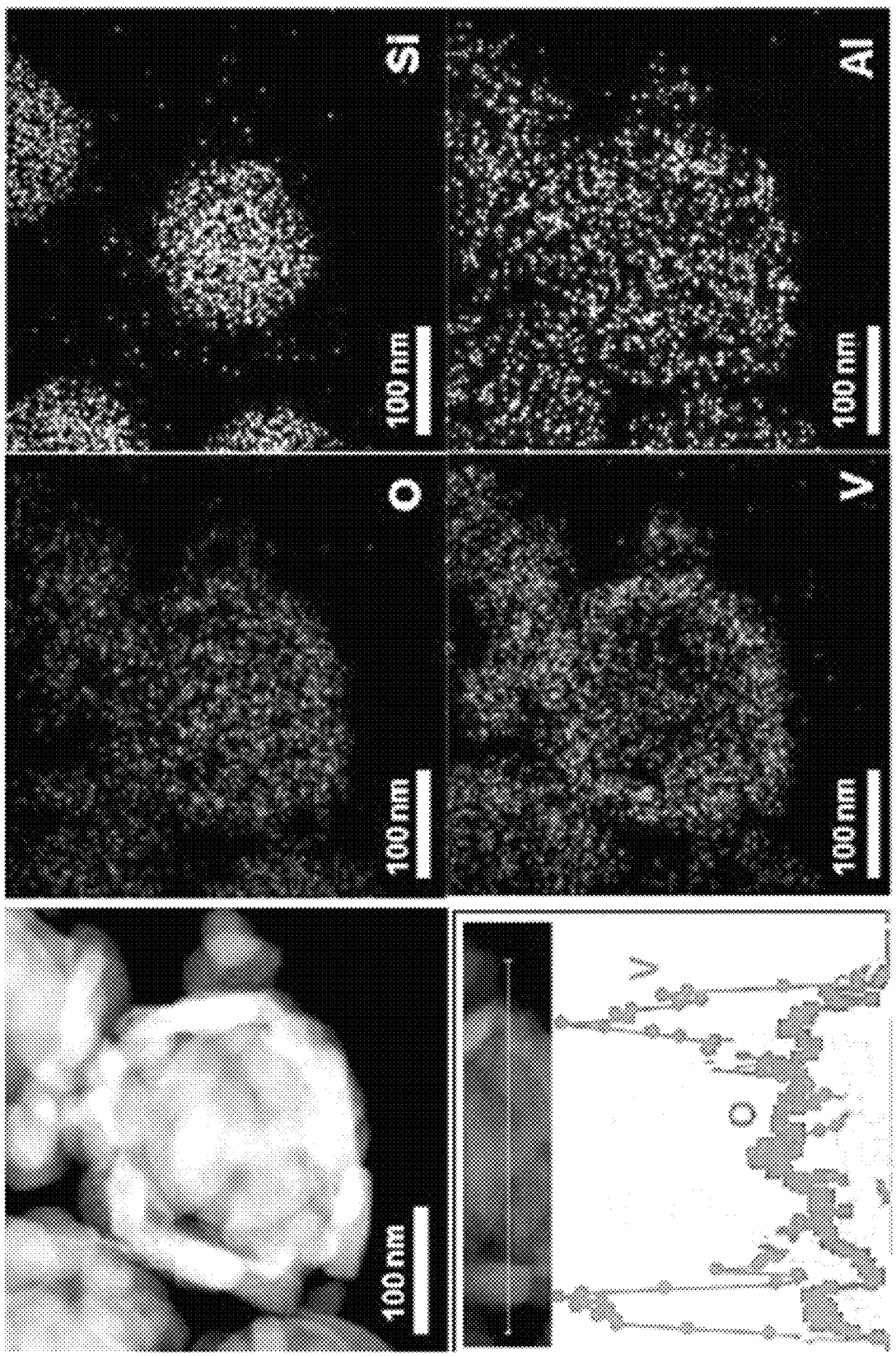
FIG. 2b is scanning TEM (STEM) images with a line-scan energy-dispersive X-ray spectroscopy (EDS) spectrum showing structural characterization of SiO$_2$@V$_2$O$_5$@Al$_2$O$_3$-(50) core@shell.

The surface morphology of SiO$_2$@V$_2$O$_5$@Al$_2$O$_3$-(50) core@shell nanostructures was investigated by SEM, scanning TEM (STEM), and EDS. FIG. 2a clearly demonstrates that outer Al$_2$O$_3$ layers were homogeneously deposited on the entire surface of SiO$_2$@V$_2$O$_5$ nanostructures. STEM imaging and the corresponding elemental mappings with EDS line scanning (FIG. 2b) displayed that O and V (derived from V$_2$O$_5$) were uniformly dispersed in the shell, while Si (derived from silica spheres) was mainly located in the core. Moreover, the distribution of alumina over the whole core@shell nanostructures demonstrated that they were coated by thin Al$_2$O$_3$ shell layers. SiO$_2$@V$_2$O$_5$@Al$_2$O$_3$-(10, 30, 50, and 100) core@shell nanostructures were also characterized by high resolution TEM, which revealed that 100 ALD cycles were sufficient to obtain full coverage by 20-nm-thick Al$_2$O$_3$ layers, while 10 cycles did not suffice for an effective coating.

Figure 3A:
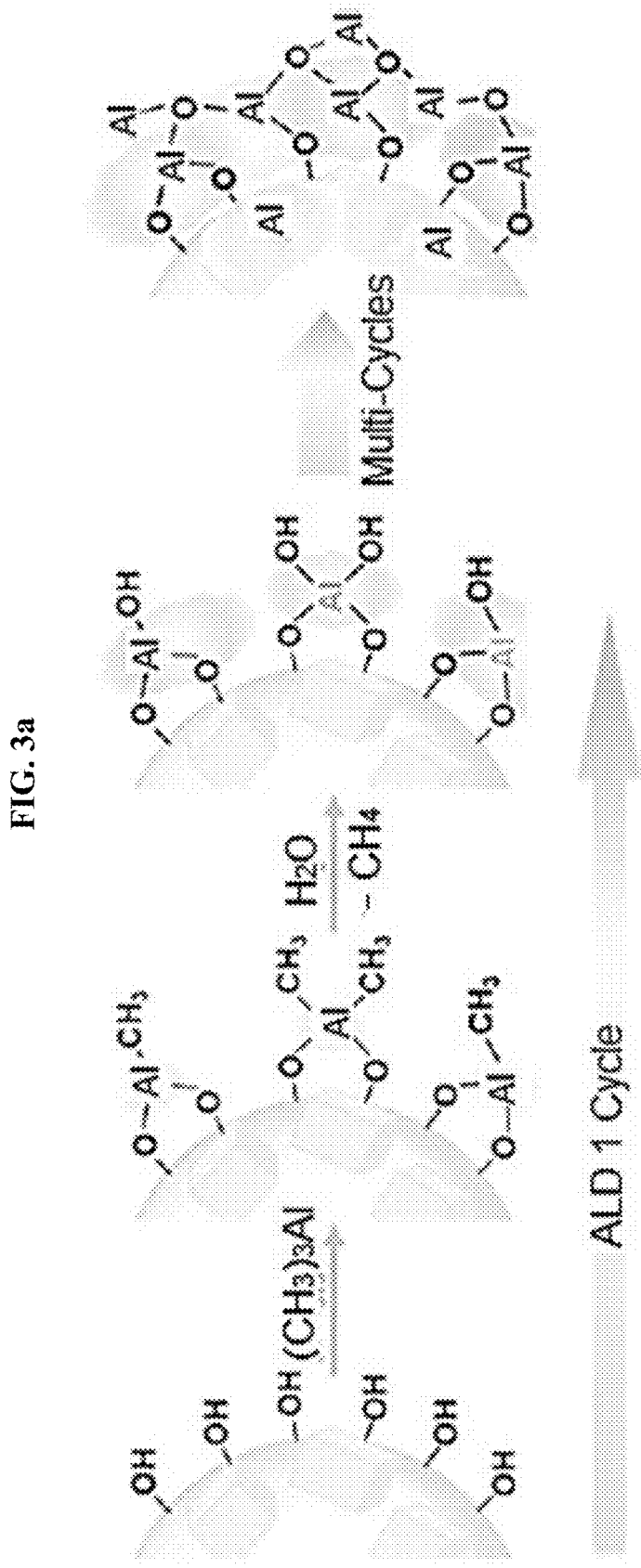
FIG. 3a is a schematic illustration of the ALD process used for multi-cycle coating of Al$_2$O$_3$ shells on SiO$_2$@V$_2$O$_5$ nanostructures.
Figure 3B:
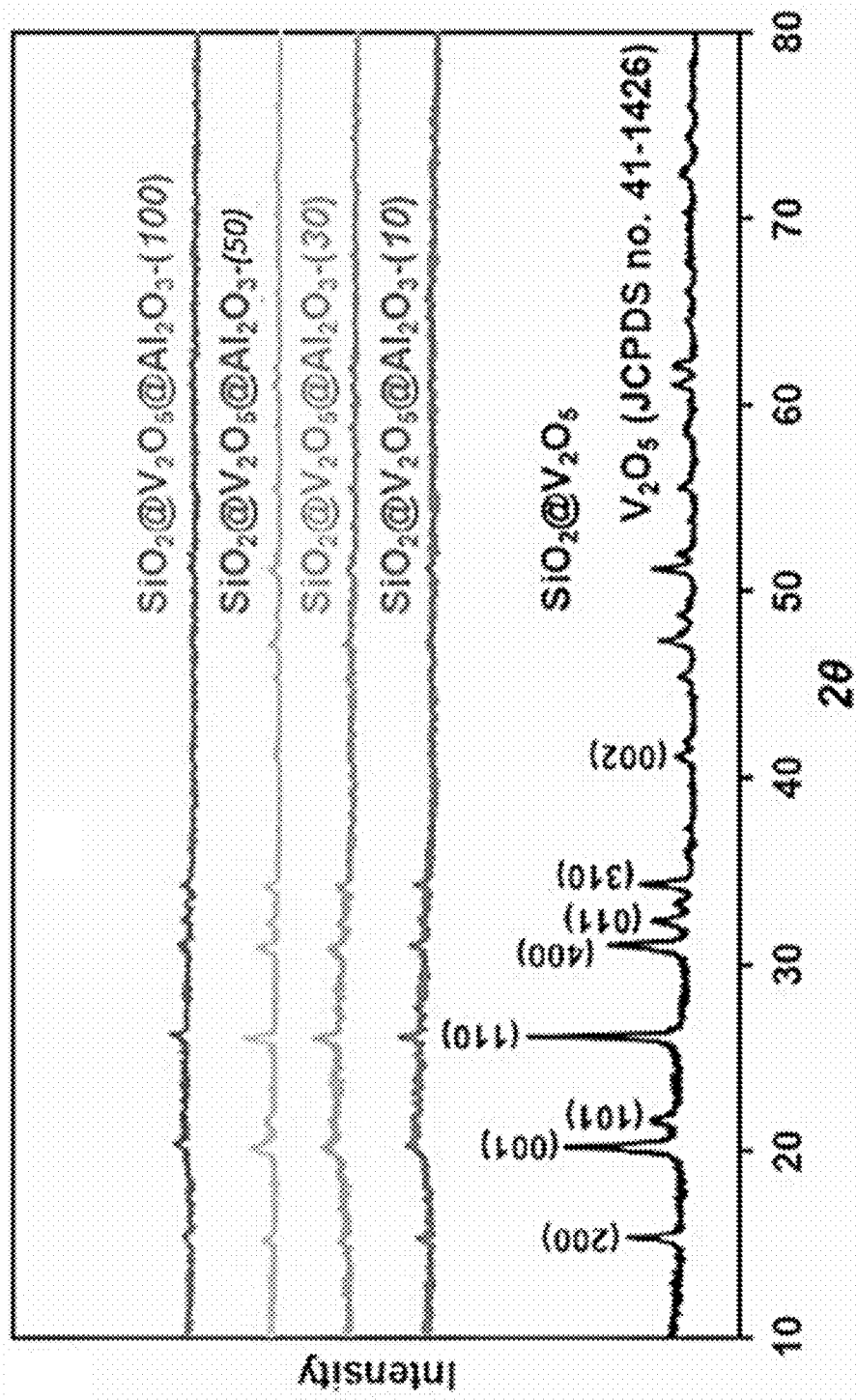
FIG. 3b shows X-ray diffraction (XRD) patterns of SiO$_2$@V$_2$O$_5$@Al$_2$O$_3$-(10, 30, 50, and 100) nanostructures.

The shell thickness of SiO$_2$@V$_2$O$_5$@Al$_2$O$_3$ core@shell nanostructures increased with the number of ALD cycles (FIG. 3a). The introduced TMA precursor was adsorbed on V$_2$O$_5$ surfaces to create Al—O bonds, and Al(OH)$_4$ units were finally produced upon the addition of water vapor. Subsequent ALD cycles resulted in the deposition of additional alumina layers over SiO$_2$@V$_2$O$_5$. The XRD patterns of SiO$_2$@V$_2$O$_5$ core@shell catalysts (FIG. 3b) revealed the presence of characteristic peaks of V$_2$O$_5$ (Pmmn, a=1.1516, b=0.3566, c=0.4372 nm). Application of the Scherrer equation to the (110) peak allowed the crystallite size of SiO$_2$@V$_2$O$_5$ core@shell structures to be estimated as 40.1 nm, which agreed with values obtained by TEM and SEM. However, much weaker XRD peaks were observed for SiO$_2$@V$_2$O$_5$@Al$_2$O$_3$ core@shell nanostructures (FIG. 3b), since the Al$_2$O$_3$ shell was not crystalline. XRD analysis of SiO$_2$@V$_2$O$_5$@Al$_2$O$_3$-(10, 30, 50, and 100) nanostructures revealed that as the number of ALD cycles increased from 10 to 100, the crystallite size (calculated as mentioned above) increased from 31.3 to 34.6 nm. From the results, (a) as-prepared V$_2$O$_5$ nanoparticles diffused to Al$_2$O$_3$ surfaces with decreased sizes of V$_2$O$_5$ and (b) X-ray diffraction from the V$_2$O$_5$ core exhibited a decreased intensity of peak because of Al$_2$O$_3$ shells obtained after an increased number of ALD cycles.

Figure 4A:
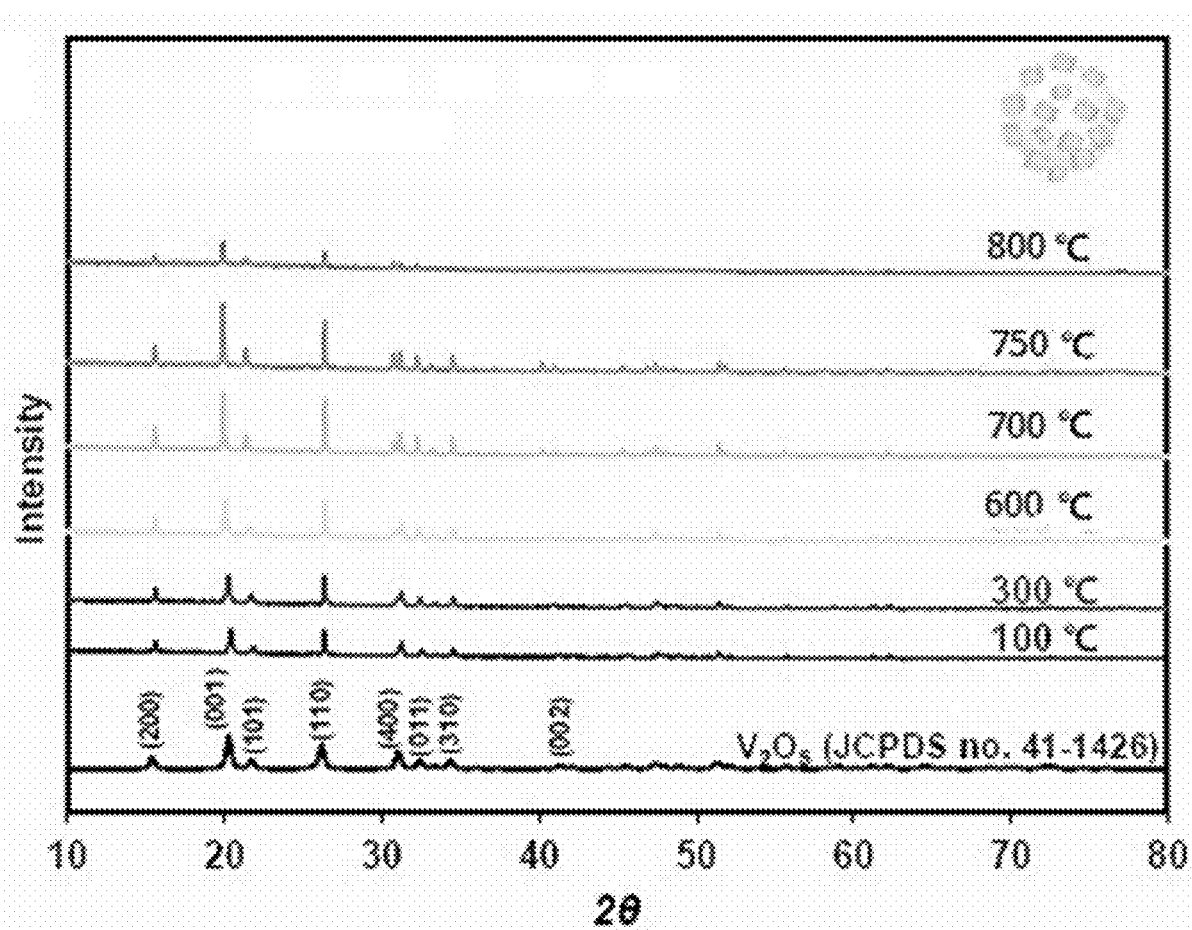
FIG. 4a and FIG. 4b show in situ XRD patterns of SiO$_2$@V$_2$O$_5$ and SiO$_2$@V$_2$O$_5$@Al$_2$O$_3$-(50) nanostructures, respectively.
Figure 4B:
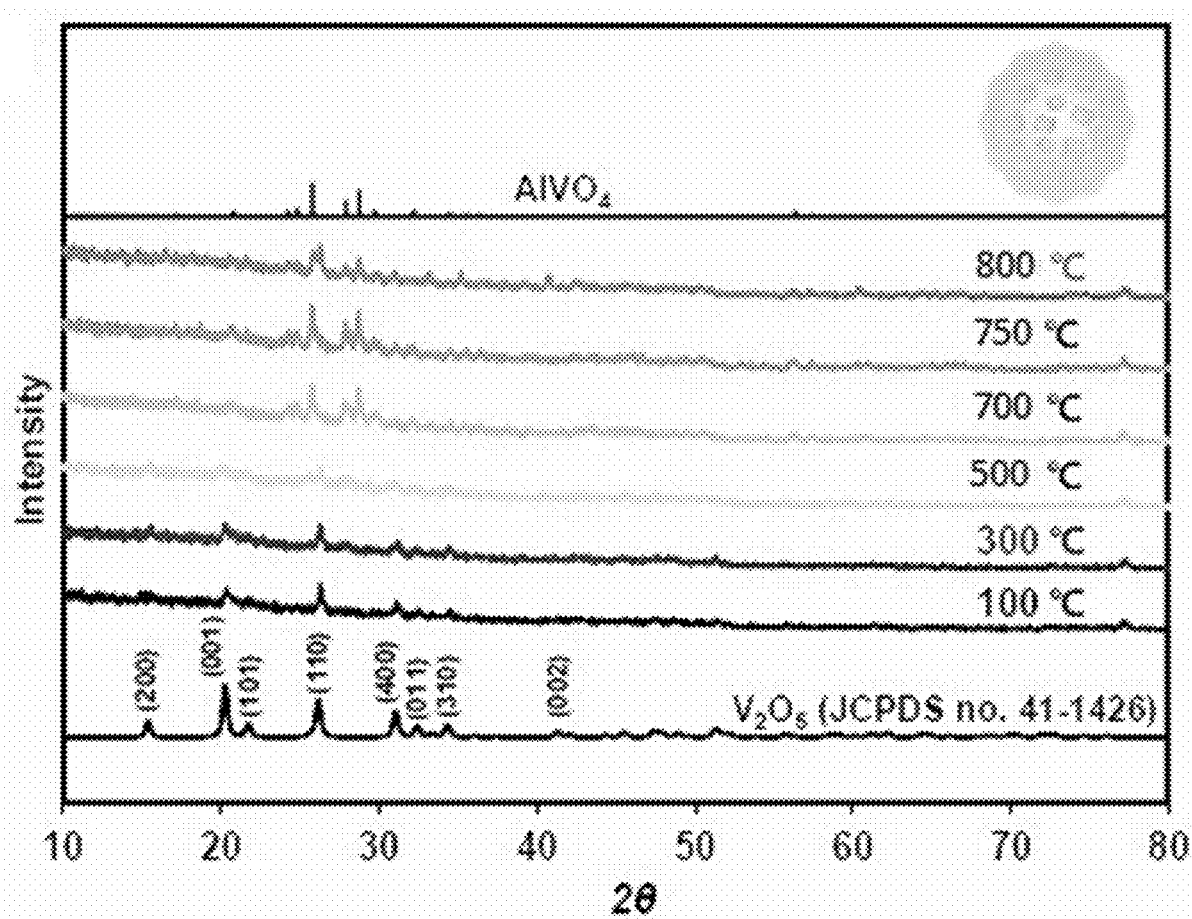

<Experimental Example 2> Thermal Stability of V$_2$O$_5$ Species in Core@Shell Nanostructures The thermal stability of SiO$_2$@V$_2$O$_5$ core@shell catalysts before/after Al$_2$O$_3$ deposition was probed by in situ XRD analysis at 100-800° C. in an atmosphere of 4% CH$_4$, 4% O$_2$, and balance Ar. FIG. 4a shows that the characteristic XRD peaks of V$_2$O$_5$ were preserved in SiO$_2$@V$_2$O$_5$ core@shells, while the peak intensity increased with increasing temperature up to 750° C. The crystallite size calculated by the Scherrer equation for V$_2$O$_5$ nanoparticles increased from 50.8 nm at 100° C. to 77.9 nm at 750° C. At high temperature, the outer V$_2$O$_5$ nanoparticles gradually collapsed. Above 800° C., structural dissociation decreased XRD peak resolution, and only the main peaks were observed. Conversely, SiO$_2$@V$_2$O$_5$@Al$_2$O$_3$-(50) core@shell nanostructures maintained their XRD peak intensities up to 800° C., which demonstrated that the presence of Al$_2$O$_3$ shells prevented the aggregation of core V$_2$O$_5$ nanoparticles at high temperature (FIG. 4b).

Interestingly, new peaks are recognized in SiO$_2$@V$_2$O$_5$@Al$_2$O$_3$ core@shell nanostructures beyond 700° C. (FIG. 4b). When the possibility of any other crystalline structure of either alumina or vanadium oxide was examined, however those were matched to neither crystalline aluminas such as alpha, gamma, and theta, nor vanadium oxides including V$_2$O$_3$, V$_4$O$_7$, and VO$_2$ and the high-resolution TEM images, show that the thin Al$_2$O$_3$ shell did not show any crystallinity. Previous studies reported that AlVO$_4$ phase formed from a solid-state reaction between V$_2$O$_5$ and Al$_2$O$_3$ beyond 570° C. and the additional XRD peaks in the range of 26–30° corresponded to the characteristic peaks of AlVO$_4$. Based on these results, as the temperature increased, thin alumina shells were not crystallized but new AlVO$_4$ species was generated resulting from a solid-state reaction between V$_2$O$_5$ and Al$_2$O$_3$ above 700° C.

<Experimental Example 3> Catalytic Oxidation of Methane to Formaldehyde

Figure 5A:
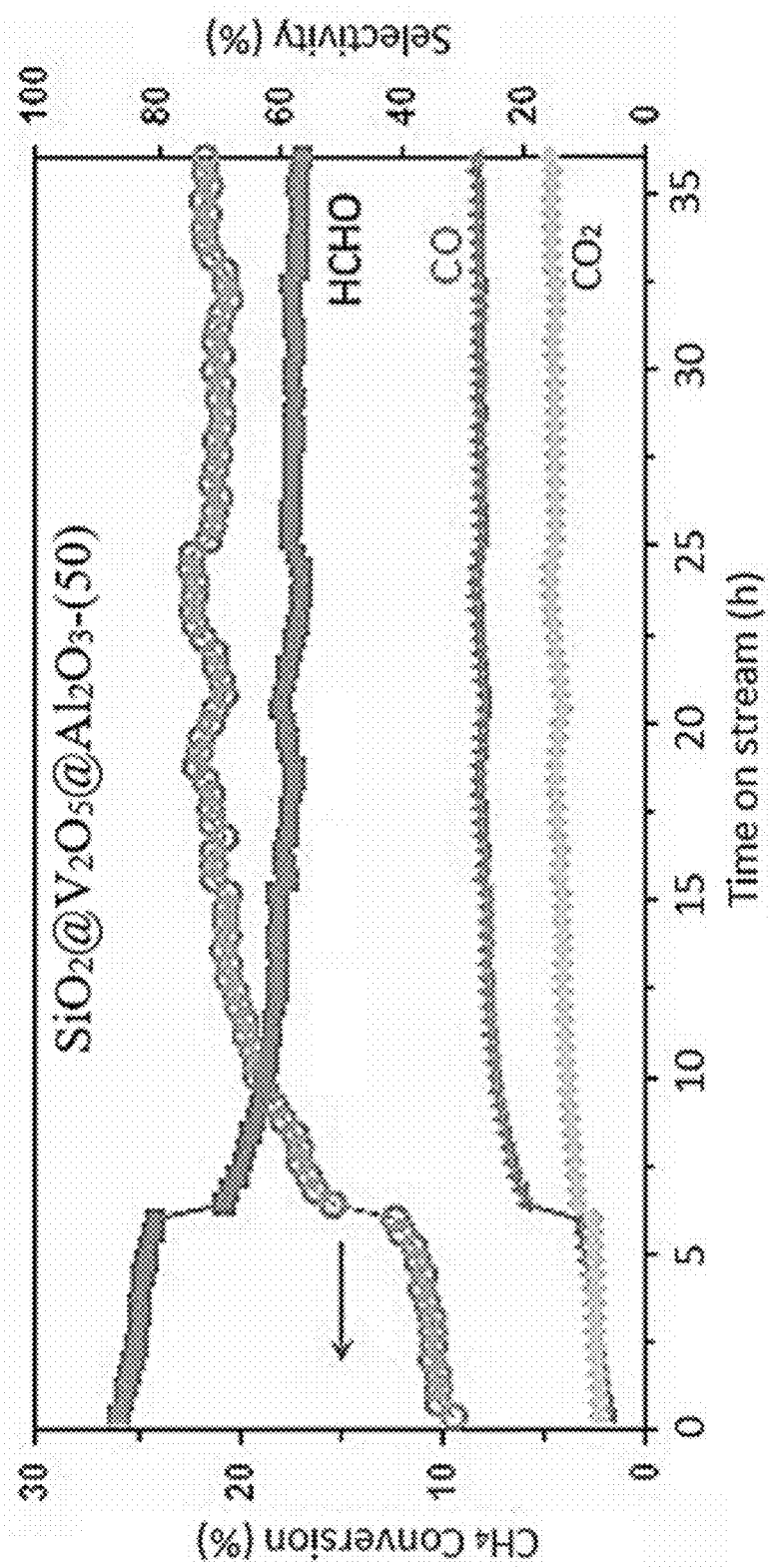
FIG. 5a shows methane oxidation performances of various SiO$_2$@V$_2$O$_5$@Al$_2$O$_3$ core@shell nanostructures and supported V$_2$O$_5$/m-SiO$_2$ catalysts at 600° C. in term of methane conversion and selectivity obtained for SiO$_2$@V$_2$O$_5$@Al$_2$O$_3$-(50) nanostructures as a function of time-on stream.

Methane oxidation over SiO$_2$@V$_2$O$_5$@Al$_2$O$_3$ core@shell nanostructures with controlled Al$_2$O$_3$ shell thickness was carried out in a laboratory-scale flow reactor operated at 600° C. at a CH$_4$/O$_2$ ratio of 1:1 (v/v). FIG. 5a shows methane conversion as a function of time-on stream over SiO$_2$@V$_2$O$_5$@Al$_2$O$_3$-(50) nanostructures at 600° C.

Figure 5B:
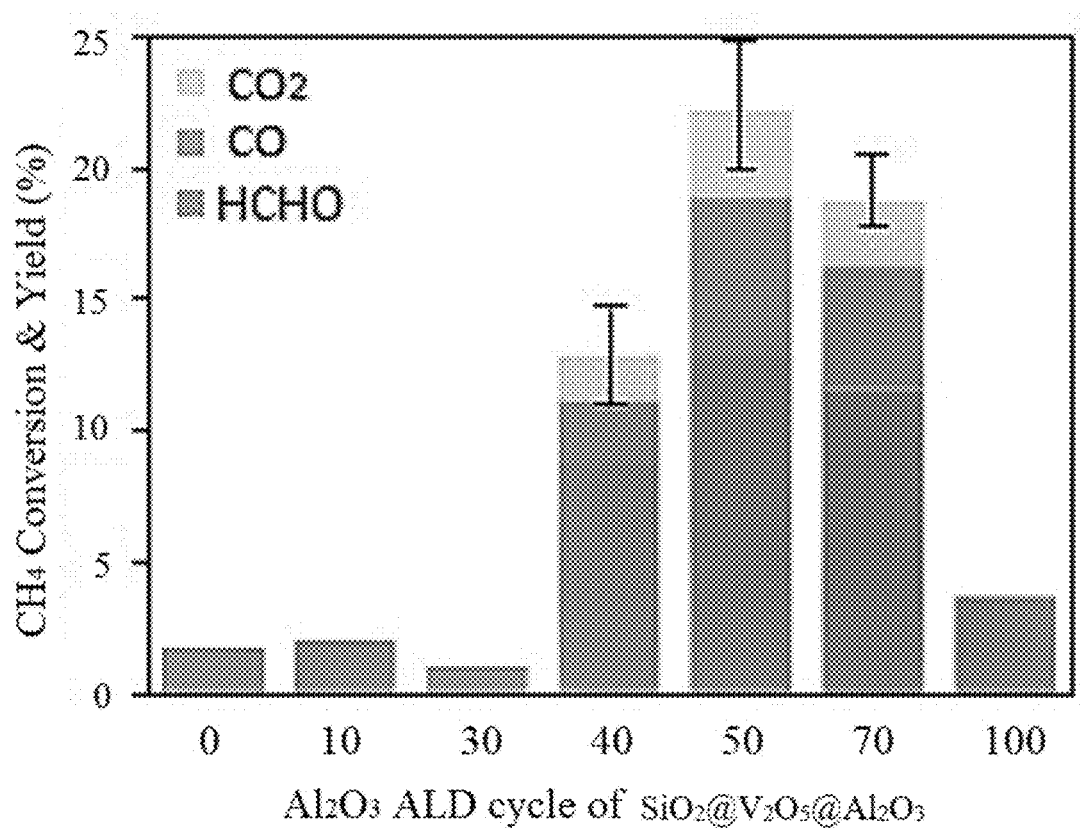
FIG. 5b shows comparison of SiO$_2$@V$_2$O$_5$@Al$_2$O$_3$-(x) core@shell nanostructures in terms of achieved methane conversion and product yield.

The initially observed gradual increase of conversion with time-on-stream was followed by an abrupt change at 6 h (at which point the product selectivity changed as well) and subsequent saturation to the maximum, which was ascribed to a structural rearrangement of the catalyst. Methane conversion of the SiO$_2$@V$_2$O$_5$@Al$_2$O$_3$-(50) nanostructures reached ~22.2%, and the corresponding HCHO, CO, and CO$_2$ selectivities equaled 57.8, 27.4, and 14.8%, respectively (FIG. 6). Beyond 35 h, the overall conversion and selectivity stayed constant, demonstrating that the SiO$_2$@V$_2$O$_5$@Al$_2$O$_3$-(50) nanostructures were thermally stable by having long-term stability in the high temperature methane oxidation. Additionally, methane oxidation was conducted over SiO$_2$@V$_2$O$_5$@Al$_2$O$_3$-(x) nanostructures having different shell thicknesses (FIG. 5b). Notably, whereas the maximum conversion of methane observed for SiO$_2$@V$_2$O$_5$@Al$_2$O$_3$ (50) equaled 22.2%, negligible conversions were observed for x=0-30. Thus, the original SiO$_2$@V$_2$O$_5$ core@shell structures did not show substantial methane oxidation activity because of the instability of V$_2$O$_5$ nanoparticles at 600° C. The protective effect of the Al$_2$O$_3$ shell was maximized in SiO$_2$@V$_2$O$_5$@Al$_2$O$_3$-(50), which featured strongly enlaced Al$_2$O$_3$ shells that still provided enough space for constant exchange of reactants and products, with further shell thickness increases resulting in deteriorated performance, e.g., a conversion of only 3.7% was observed for SiO$_2$@V$_2$O$_5$@Al$_2$O$_3$-(100) (FIG. 5b and FIG. 6). FIG. 5c shows the methane oxidation performance of V$_2$O$_5$/m-SiO$_2$ catalysts with vanadium loadings of 1, 3, and 5 wt %, revealing that methane conversions (5.5-5.6%) and HCHO selectivities (65.7-71.2%) obtained at 600° C. were in good agreement with the previous research. FIG. 6 summarizes the methane oxidation performances of core@shell nanostructures with controlled $Al_2O_3$ shell thicknesses and those of supported $V_2O_5$/M-S102 catalysts, demonstrating that the best methane conversion achieved for $SiO_2@V_2O_5@Al_2O_3$-(50) achieved has never achieved before for any vanadium-based catalyst at 600° C.

Therefore, the $SiO_2@V_2O_5@Al_2O_3$-(50) nanostructure of the present invention exhibited the best catalytic activity with $CH_4$ conversion of 22.2% and HCHO selectivity of 57.8% under 24,000 mL $g_{cat}^{-1}$ $h^{-1}$ at 600° C., over all the vanadium-based catalysts that convert known methane to HCHO.

<Experimental Example 4> Characterization of $V_2O_5$ in $SiO_2@V_2O_5@Al_2O_3$ Core@Shell Catalysts The catalytic activity of supported vanadium catalysts is known to depend on the dispersion of vanadium, the nature of vanadium active sites, and the metal-support interaction determined by the selection of suitable oxide supports. For many catalytic oxidations, including the partial oxidation of hydrocarbons, oxidative dehydrogenation of alkanes to alkenes, selective catalytic reduction of $NO_x$, and the oxidation of $SO_2$, isolated tetrahedral ($T_d$) vanadium oxide species containing terminal V=O groups have been proposed as active sites. To characterize vanadium species in $SiO_2@V_2O_5@Al_2O_3$ core@shell nanostructures and compare them to those in $V_2O_5$/m-$SiO_2$ catalysts, the above materials were analyzed by Raman spectroscopy, $H_2$-TPR, and diffuse reflectance UV-vis spectroscopy.

Figure 7A:
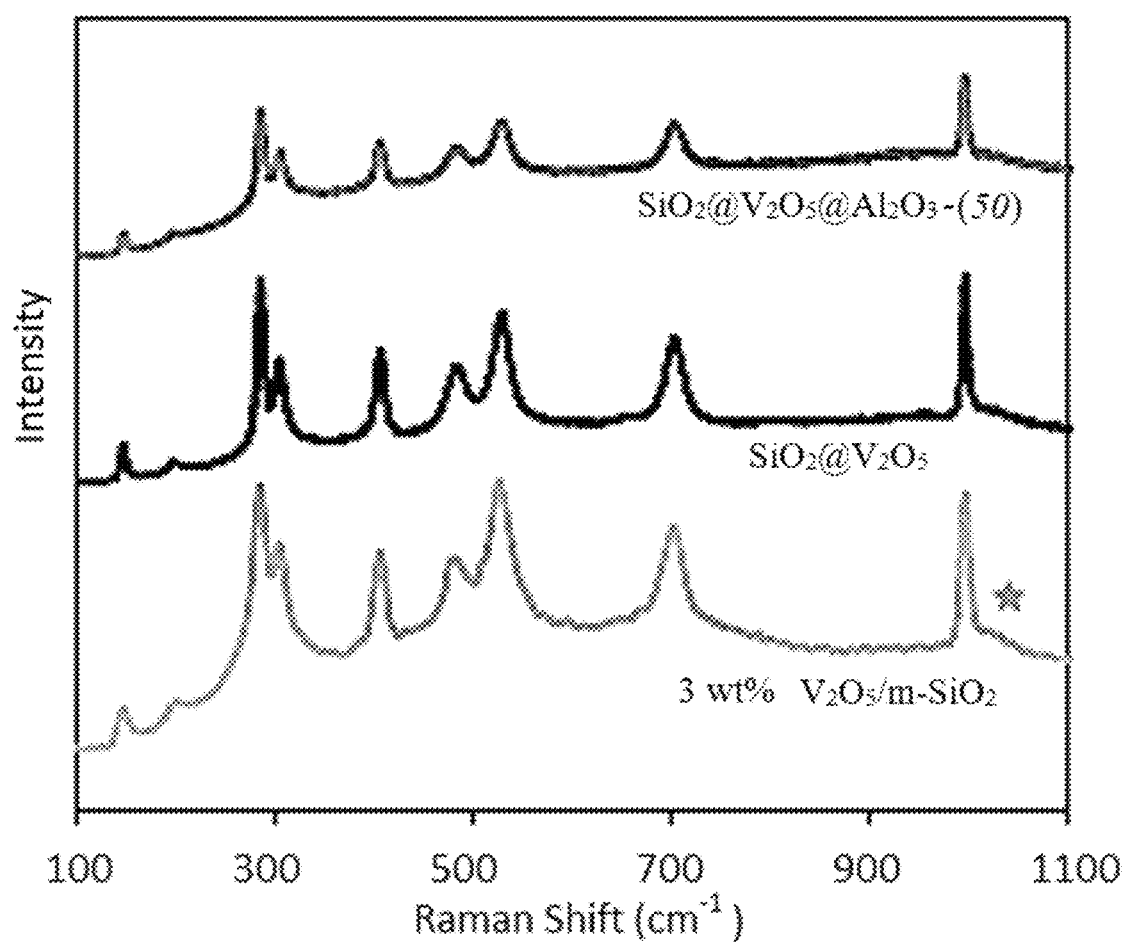
FIG. 7a, FIG. 7b, and FIG. 7c show Raman spectra, H$_2$ temperature programmed reduction (H$_2$-TPR) curves, and UV-vis diffuse reflectance spectra of SiO$_2$@V$_2$O$_5$ and SiO$_2$@V$_2$O$_5$@Al$_2$O$_3$-(50) core@shell nanostructures, and 3 wt % V$_2$O$_5$/m-SiO$_2$, respectively.

FIG. 7a shows Raman spectra of $V_2O_5$/m-$SiO_2$ and $SiO_2@V_2O_5@Al_2O_3$-(50) core@shell nanostructures at 600° C., revealing the presence of bands at 995 (V=0), 703, 406, 305, and 285 cm' in all cases and thus indicating that all catalysts contained crystalline $V_2O_5$. Although the Raman spectra of 3 wt % $V_2O_5$/m-$SiO_2$ were similar to those of core@shell catalysts prepared from crystalline $V_2O_5$, a shoulder peak at 1040 cm' ascribed to the symmetric V=O stretch of isolated $VO_4$ species was observed in the former case (FIG. 7a). Interestingly, as the vanadium content of $V_2O_5$/m-$SiO_2$ decreased to 1 wt %, the above shoulder peak became dominant, which indicated that the relative content of crystalline $V_2O_5$ in $V_2O_5$/m-$SiO_2$ catalysts decreased at low vanadium loadings.

Figure 7B:
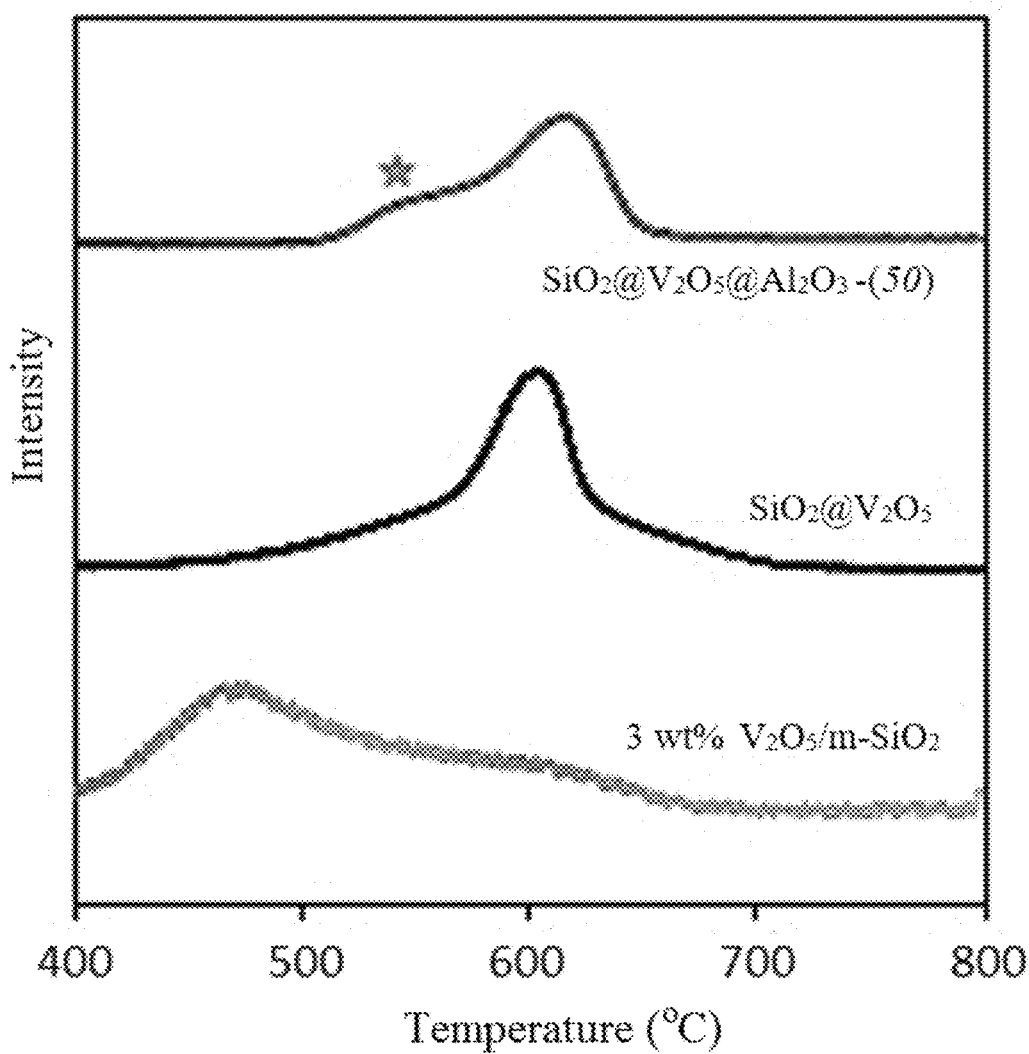

The dispersion and type of active vanadium species were evaluated by $H_2$-TPR. In previous reports, the low-temperature $H_2$-TPR reduction peak observed at 460-500° C. was ascribed to the reduction of $V^{5+}$ in highly dispersed monomeric species to $V^{3+}$. As the vanadium loading increased, the reduction peaks shifted to higher temperatures as a consequence of reduction kinetics. The high-temperature reduction peak at ~600° C. was assigned to the reduction of vanadium in polymeric and bulk-like $V_2O_5$ species. The TPR profiles in FIG. 7b show that 3 wt % $V_2O_5$/m-$SiO_2$ contained highly disperse monomeric species as well as a small amount of $V_2O_5$ species, in good agreement with the results of Raman spectroscopy analysis. Pristine $SiO_2@V_2O_5$ contained only bulk $V_2O_5$ species, which was ascribed to the size of $V_2O_5$ nanoparticles (35 nm). Conversely, the $SiO_2@V_2O_5@Al_2O_3$ (50) core@shell catalyst contained both $V_2O_5$ and highly disperse monomeric species, exhibiting two broad TPR bands at 550 and 620° C.

Figure 7C:
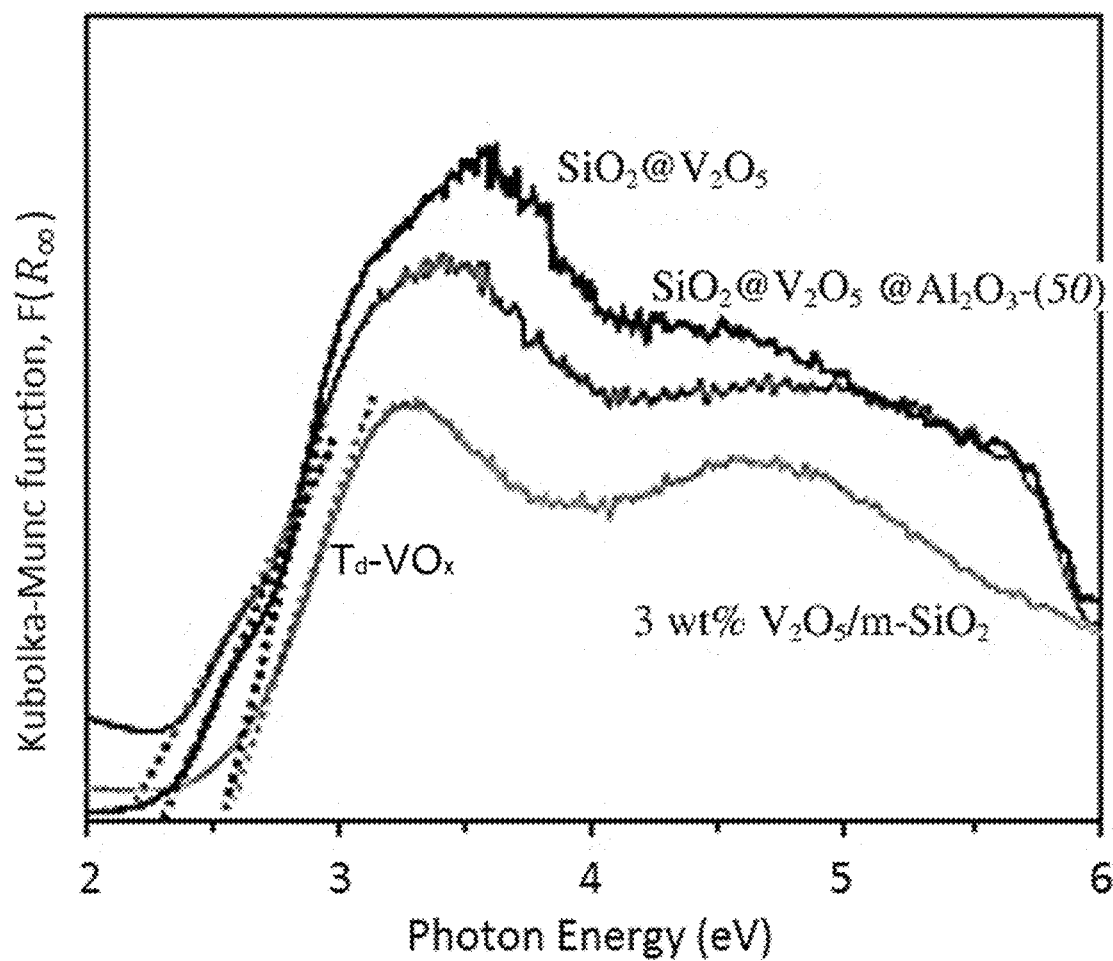

Finally, the dispersion of the vanadium-based catalyst and the active species structure were analyzed using a diffuse reflectance UV-vis spectrometer (FIG. 7c). The absorption band just above 3 eV was ascribed to $VO_x$ species with $T_d$ coordination, while that around 5.5 eV evidenced the presence of monomeric $T_d$ species. The absorption edge positions of 3 wt % $V_2O_5$/m-$SiO_2$ (2.6 eV) and $SiO_2@V_2O_5$/ $SiO_2@V_2O_5@Al_2O_3$-(50) (<2.4 eV) indicated that the former catalyst contained homogeneous $T_d VO_x$ species with a smaller domain size than those of the other two catalysts. The low-energy shoulder observed for core@shell catalysts comprising 35-nm $V_2O_5$ nanoparticles was ascribed to the bimodal size distribution of crystalline $V_2O_5$ species that was not observed for $V_2O_5$/m-$SiO_2$. Furthermore, the size distributions deduced from shoulder peaks were different for $SiO_2@V_2O_5$ and $SiO_2@V_2O_5@Al_2O_3$-(50) core@shell catalysts, demonstrating that the properties of crystalline $V_2O_5$ species are changed by the deposition of $Al_2O_3$ shells.

Since the interaction between $V_2O_5$ and $Al_2O_3$ influenced on the catalytic performance, methane oxidation was performed over conventional $V_2O_5$/$Al_2O_3$ catalysts. When $V_2O_5$/$Al_2O_3$ catalysts were prepared by the impregnation with different vanadium loading of 3 and 5 wt % and tested the reaction, negligible conversions were obtained (less than 2% of methane conversion) for both catalysts. These results were agreement with the previously conducted study.

Figure 7D:
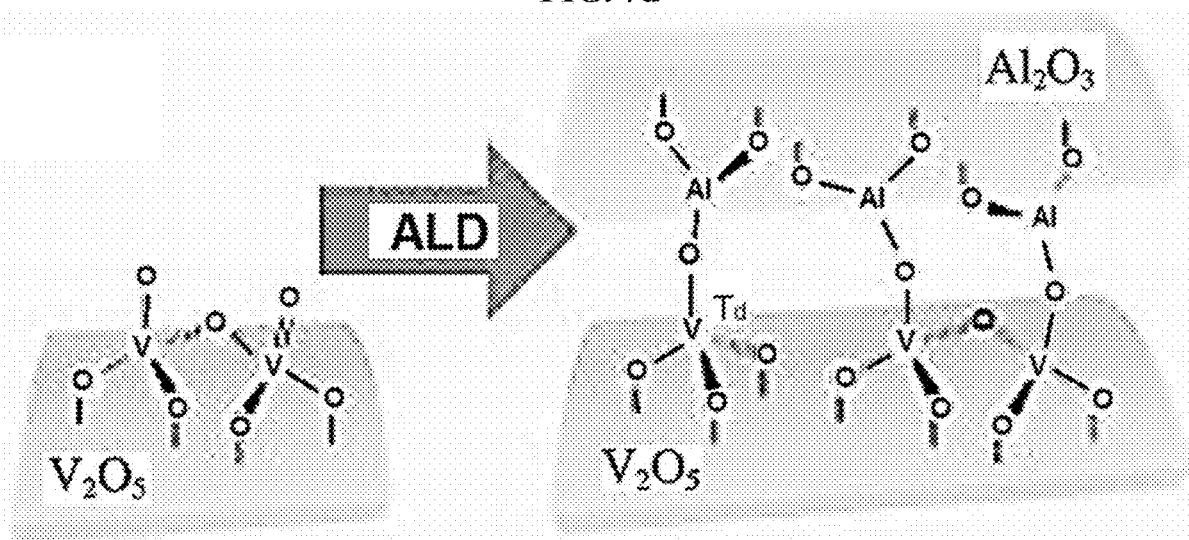
FIG. 7d shows a formation of new T$_d$ vanadium species and V—O—Al bonds by a reaction between V$_2$O$_5$ and Al$_2$O$_3$ in the SiO$_2$@V$_2$O$_5$@Al$_2$O$_3$ core@shell catalyst.

From the above results, the $V_2O_5$ nanoparticles formed on the spherical $SiO_2$ particles were identified as crystalline $V_2O_5$ species, and the $Al_2O_3$ shell of $SiO_2@V_2O_5@Al_2O_3$-(50) promoted the interaction between $V_2O_5$ and $Al_2O_3$ during the ALD process, (FIG. 7d). Based on the fact that the $AlVO_4$ phase is present in the $SiO_2@V_2O_5@Al_2O_3$ core@shell nanostructure at elevated temperatures, the interaction between $V_2O_5$ nanoparticles and $Al_2O_3$ creates a bridging VO—Al bond in $AlVO_4$. Highly dispersed $T_d$ vanadium species with V—O—Al bonds in $SiO_2@V_2O_5@Al_2O_3$ core@shell nanostructures did not appear in conventional $V_2O_5$/$Al_2O_3$ catalysts.

In conclusion, newly formed $T_d$ monomer vanadium species connected to V—O—Al bond could be used for methane oxidation reaction at 600° C. to obtain high methane conversion. In addition, the $Al_2O_3$ shell also protected the $V_2O_5$ nanoparticles from firing, and obtained a thermal stability effect.

The invention claimed is:

1. A catalyst for methane oxidation comprising:
   a core structure consisting of a nano-support comprising $SiO_2$ and core nanoparticles comprising $V_2O_5$; and
   a shell coating layer comprising $Al_2O_3$ coated on the core structure,
   wherein the core nanoparticles have a particle diameter smaller than that of the nano-support and are coated on the nano-support to form a core structure.

2. The catalyst for methane oxidation of claim 1, wherein the $SiO_2$ is a spherical $SiO_2$.

3. The catalyst for methane oxidation of claim 1, wherein the $V_2O_5$ has an average particle size of 10 to 100 nm.

4. A method of preparing the catalyst for methane oxidation of claim 1 comprising:
   preparing a nano-support comprising $SiO_2$;
   preparing a core structure by hydrothermal reaction of $V_2O_5$ nanoparticles on the nano-support; and
   forming a core-shell nanostructure by atomic layer deposition of $Al_2O_3$ on the core structure.

5. The method of preparing the catalyst for methane oxidation of claim 4, wherein the nano-support is spherical nano-support.

6. The method of preparing a catalyst for methane oxidation of claim 4, wherein the hydrothermal reaction is performed at 100 to 250° C. for 5 to 30 hours.

7. The method of preparing a catalyst for methane oxidation of claim 4, wherein the atomic layer deposition is performed for 1 to 100 cycles using trimethylaluminum and $H_2O$.

8. A catalyst for methane oxidation, which is prepared by the method of preparing the catalyst for methane oxidation of claim 4.

9. A method of methane oxidation, comprising reacting methane and oxygen in the presence of the catalyst for methane oxidation of claim 1.

10. A method of methane oxidation for producing formaldehyde comprising producing formaldehyde by reacting methane and oxygen at 500 to 800° C. in the presence of the catalyst for methane oxidation of claim 1.

11. A method of methane oxidation, comprising reacting methane and oxygen in the presence of the catalyst for methane oxidation of claim 8.

12. A method of methane oxidation for producing formaldehyde comprising producing formaldehyde by reacting methane and oxygen at 500 to 800° C. in the presence of the catalyst for methane oxidation of claim 8.

13. The catalyst for methane oxidation of claim 1, wherein the catalyst has a $SiO_2@V_2O_5@Al_2O_3$-(x) (x=10, 30, 40, 50, 70, and 100) core@shell nanostructure.

14. The catalyst for methane oxidation of claim 1, wherein the catalyst has a $SiO_2@V_2O_5@Al_2O_3$-(x) (x=40–70) core@shell nanostructure.

15. The catalyst for methane oxidation of claim 1, wherein the catalyst has a $SiO_2@V_2O_5@Al_2O_3$-(x) (x=40, 50, 70) core@shell nanostructure.

* * * * *